United States Patent
Kanik et al.

(10) Patent No.: US 9,585,632 B2
(45) Date of Patent: Mar. 7, 2017

(54) ESTIMATION OF A MECHANICAL PROPERTY OF ANATOMY FROM MEDICAL SCAN DATA

(71) Applicants: Jingjing Kanik, Hamden, CT (US); Puneet Sharma, Monmouth Junction, NJ (US); Tommaso Mansi, Plainsboro, NJ (US); Razvan Ionasec, Nuremberg (DE); Ali Kamen, Skillman, NJ (US); Dorin Comaniciu, Princeton Junction, NJ (US); James S. Duncan, Madison, CT (US)

(72) Inventors: Jingjing Kanik, Hamden, CT (US); Puneet Sharma, Monmouth Junction, NJ (US); Tommaso Mansi, Plainsboro, NJ (US); Razvan Ionasec, Nuremberg (DE); Ali Kamen, Skillman, NJ (US); Dorin Comaniciu, Princeton Junction, NJ (US); James S. Duncan, Madison, CT (US)

(73) Assignees: SIEMENS MEDICAL SOLUTIONS USA, INC., Malvern, PA (US); YALE UNIVERSITY, New Haven, CT (US)

(*) Notice: Subject to any disclaimer, the term of this patent is extended or adjusted under 35 U.S.C. 154(b) by 384 days.

(21) Appl. No.: 14/259,801

(22) Filed: Apr. 23, 2014

(65) Prior Publication Data
US 2015/0305706 A1    Oct. 29, 2015

(51) Int. Cl.
*A61B 8/00* (2006.01)
*A61B 8/08* (2006.01)

(52) U.S. Cl.
CPC .......... *A61B 8/0883* (2013.01); *A61B 8/5223* (2013.01); *A61B 8/5276* (2013.01)

(58) Field of Classification Search
CPC ..... G06T 7/206; G06T 7/0016; G06T 7/2046; A61B 5/0263; A61B 8/08; A61B 8/0883; A61B 5/5276; A61B 8/5223
See application file for complete search history.

(56) References Cited

U.S. PATENT DOCUMENTS

| | | |
|---|---|---|
| 8,009,887 B2 | 8/2011 | Ionasec et al. |
| 8,224,640 B2 | 7/2012 | Sharma et al. |
| 8,527,251 B2 | 9/2013 | Ionasec et al. |
| 2010/0240996 A1 | 9/2010 | Ionasec et al. |

(Continued)

OTHER PUBLICATIONS

Schneider, R. et al., "Patient-specific mitralleaflet segmentation from 4D ultrasound," Medical Image Computing and Computer-Assisted Intervention, MICCAI 2011, Springer, pp. 520-527.

(Continued)

*Primary Examiner* — Joel Lamprecht

(57) ABSTRACT

A mechanical property of anatomy is estimated from a patient in vivo, such as estimating a patient-specific material property of a valve. A morphological model is used to determine anatomy dynamics. A biomechanical model, using the anatomy dynamics, predicts the dynamics, based, at least in part, on one or more material properties. Using an inverse solution based on comparison of dynamics predicted by the biomechanical model and the dynamics determined from the morphological model, values for the material properties are determined.

20 Claims, 3 Drawing Sheets

(56) References Cited

U.S. PATENT DOCUMENTS

2014/0071125 A1* 3/2014 Burlina ............... G06T 7/2033
 345/420

OTHER PUBLICATIONS

Ionasec RI. et al., "Patient-Specific Modeling and Quantification of the Aortic and Mitral Valves From 4-D Cardiac CT and TEE," IEEE Trans. Med. Imaging 29(9), pp. 1636-1651, 2010.

Voigt, I. et al., "Robust physically-constrained modeling of the mitral valve and subvalvular apparatus," Medical Image Computing and Computer-Assisted Intervention. MICCAI 2011, Springer, pp. 504-511.

Kunzelman, K. et al., "Material Characterization and Biological Evaluation of Calcium Pyrophosphates for Use as Bone Graft Substitutes," Dissertation Abstracts, The University of Texas Southwestern Medical Center at Dallas and the University of Texas at Arlington, p. 737, Jun. 1991.

Conti, C. et al., "Mitral valve modelling in ischemic patients: Finite element analysis from cardiac magnetic resonance imaging: In: Computers in Cardiology," IEEE. pp. 1059-1062, 2010.

Q Wang et al., "Finite Element Modeling of Mitral Valve Dynamic Deformation Using Patient-Specific Multi-Slices Computed Tomography Scans," Annals of Biomedical Engineering, DOI: 10.1007/s10439-012-0620-6.

Jassar, A. et al., "Quantitative mitral valve modeling using real-time three-dimensional echocardiography: Technique and repeatability," The Annals of thoracic surgery 91, pp. 165-171, 2011.

Krishnamurthy, G. et al., "Stress-strain behavior of mitral valve leaflets in the beating ovine heart," Journal of biomechanics 42, pp. 1909-1916, 2009.

Stevanella, M. et al., "Mitral leaflet modeling: Importance of in vivo shape and material properties," Journal of biomechanics 44, pp. 2229-2235, 2011.

Mansi T. et al., "Towards Patient-Specific Finite-Element Simulation of MitralClip Procedure," MICCAI (1) 2011: pp. 452-459.

Shi P. et al., "Stochastic finite element framework for simultaneous estimation of cardiac kinematic functions and material parameters," Medical Image Analysis 7(4): pp. 445-464, 2003.

Burlina, P. et al., "Patient-specific modeling and analysis of the mitral valve using 3d-tee." In: Proc. IPCAI, pp. 135-146, 2010.

Allard, Jet al., "Sofa—an open source framework for medical simulation," 2007.

* cited by examiner

ESTIMATION OF A MECHANICAL PROPERTY OF ANATOMY FROM MEDICAL SCAN DATA

BACKGROUND

The present embodiments relate to modeling of anatomy, such as the mitral valve. Medical imaging data is used to create patient-specific modeling.

Medical imaging techniques provide powerful tools to visualize valvular structures. Echocardiography (e.g., 4D Transesophageal Echocardiography (TEE)) is used in many clinical applications because of high temporal resolution, ease of use, and relatively low cost. Advancements in imaging techniques may allow for quantitative evaluation of the mitral valve structure to aid predictive surgical planning.

Several approaches have been proposed to model mitral valve geometry and dynamics, including morphological and biomechanical models. The morphological models employ an automatic or semi-automatic method to detect the mitral apparatus and track motion from medical images. These models provide visualization and quantitative measurements of the anatomical structure, but do not provide the underlying mechanisms of the motion pattern or pathological changes.

Several patient-specific biomechanical models, including structural models and fluid-structure interaction models, have been proposed using geometric information from medical images and general (e.g., population based) material parameters of the mitral leaflet tissues from experimental results. Mechanical models describing the mechanism of mitral valve dynamics may be useful to predict how the pathological dynamics can be modified by medical intervention. Such models have the potential to become efficient predictive tools to design preoperative treatment plans in selecting the patients and determining clipping sites to ensure the optimal outcome. However, the use of general material parameters limits the representation for specific patients, resulting in the model being of less use for diagnosis and surgical planning for a given patient.

BRIEF SUMMARY

By way of introduction, the preferred embodiments described below include methods, computer readable media and systems for estimating a mechanical property of anatomy, such as estimating a patient-specific material property of a valve. A morphological model is used to determine anatomy dynamics. A biomechanical model, using the anatomy dynamics, predicts the dynamics, based, at least in part, on one or more material properties. Using an inverse solution based on comparison of dynamics predicted by the biomechanical model and the dynamics determined from the morphological model, patient-specific values for the material properties are determined.

In a first aspect, a method is provided for estimating a mechanical property of anatomy. A processor estimates first anatomy locations of a valve of a patient from first medical image data of the patient at a first time and second anatomy locations of the valve of the patient from second medical image data of the patient at a second time different than the first time. The second anatomy locations are for a same anatomy of the valve as the first anatomy locations. The processor models the valve with a biomechanical model, which is a function of the mechanical property and a displacement of the first anatomy locations to the second anatomy locations. The processor inversely solves for a value of the mechanical property of the valve as a function of the biomechanical model and a similarity of the displacement with displacement output by the biomechanical model.

In a second aspect, a non-transitory computer readable storage medium has stored therein data representing instructions executable by a programmed processor for estimating a mechanical property of anatomy. The storage medium includes instructions for deriving first motion of the anatomy from scan data of a patient, calculating a second motion of the anatomy from a biomechanical model, the biomechanical model being a function of the first motion and at least one patient-specific material parameter, comparing the second motion to the first motion, and solving, iteratively, for the patient-specific material parameter by repetition of the calculating and comparing.

In a third aspect, a system is provided for estimating a mechanical property of anatomy. An ultrasound scanner is configured to scan a heart volume of a patient, the scan providing medical diagnostic ultrasound data representing at least a part of the heart. A processor is configured to perform inverse analysis by deriving valve dynamics from the medical diagnostic ultrasound data, combining the valve dynamics with a biomechanical model, estimating the mechanical property from the combination, interpolating valve kinematics with the estimated mechanical property, and refining motion estimation with an alteration of the mechanical property. A display configured to generate a visualization of the mechanical property.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
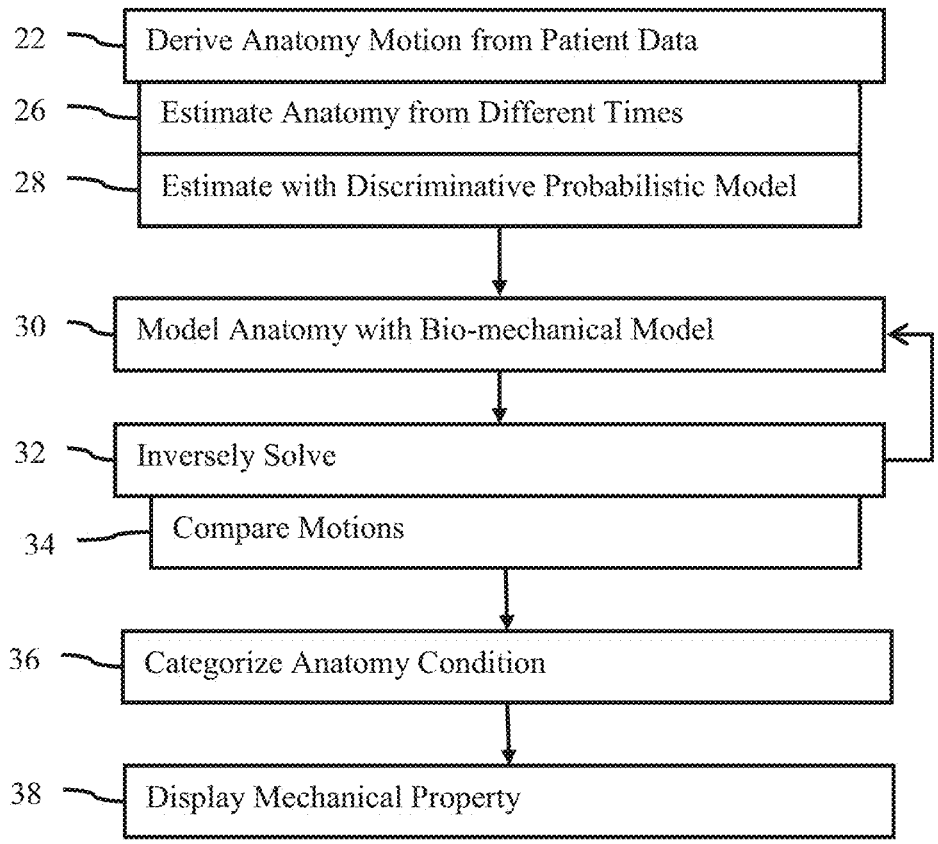
FIGS. 1-3 are flow chart diagrams of different embodiments of a method for estimating a mechanical property of anatomy.

One or more mechanical properties of anatomy, such as a mitral valve, are estimated from medical scan data of a patient. The mechanical properties are estimated for a specific patient rather than using generalized estimates. An inverse analysis framework combines image-based and biomechanical models to estimate the patient specific material property of anatomy and generate physically constrained motion. For example, the material parameters of the leaflets and the regional heterogeneity in distribution (anterior and posterior leaflets) for a given patient may be determined. The patient-specific regional material property enables the mechanical model to closely simulate, in vivo, mitral valve dynamic motion. In this way, the comprehensive patient-specific model may serve as a basis for predictive and efficient functional simulation to understand the anatomy function, design a surgical plan and assess a treatment outcome.

Any anatomy may be modeled, such as the heart, heart chamber, vessel, arteries, liver, lungs, or other part of a patient subjected to motion. In the example embodiments discussed herein, the mitral valve is used as an example. In other embodiments, more than one heart valve is identified and parameterized at a same time or during a same imaging session. For example, the mitral valve and the aortic valve are physiologically modeled. The whole heart, half the heart, or other sub-portion of the heart may be modeled.

The mitral valve is small and relatively rapidly moving. As a result, the types of imaging used to view the mitral valve may be limited, such as using ultrasound. With these limited types of imaging, it may be difficult to diagnose or plan from images alone given temporal and/or spatial resolution limitations due to the speed and small size of the mitral valve. Mechanical properties and modeling of the mitral valve may provide additional information.

In one embodiment, transesophageal echocardiography (TEE) is used to scan cardiovascular morphology for diagnosis, treatment planning and assessment and surgical guidance. The high quality four dimensional (volume over time) TEE imaging allows for the analysis of not only the geometry but also the dynamics of the mitral valve. This morphological modeling may not provide patient-specific tissue properties.

Using the TEE imaging, an inverse analysis algorithm combines image-derived mitral valve dynamics and a biomechanical model to estimate patient-specific material parameters, interpolate the underlying mechanism of mitral valve kinematics, and refine the motion estimation. The refined motion estimation is constrained by the biomechanical model with personalized material parameters, so more likely matches each patient's mitral valve function better than if a generalized material parameters were used. Physiologically significant information may be determined. The patient-specific material property enables more reliable predictive surgical simulation and treatment decision.

Patient-specific computational models including morphological and biomechanical models based on medical images may provide quantitative information to aid clinicians for mitral valve (MV) disease management. Morphological models focus on extracting geometric information by automatically detecting the mitral valve structure and tracking structure motion from medical images, such as from TEE scan data. Biomechanical models are primarily used for analyzing the underlying mechanisms of the observed motion pattern. Patient-specific biomechanical models integrate the personalized mitral apparatus and boundary conditions estimated from medical images to predicatively study the pathological changes and conduct surgical simulations. For further patient specificity, one or more material properties of the biomechanical model are determined using the inverse solution. For one approach involving the mitral valve, the algorithm achieves the customization by adjusting both the chordae rest length and other material parameters, such as Young's modulus, which are challenging to estimate or measure directly from the medical images. The algorithm first estimates the mitral valve motion from scan data using a machine learning method and then incorporates the biomechanical model generated motion into the scan data-based estimation by minimizing the Euclidean distances between the two for the inverse solution.

Material properties vary among patients, especially in diseased areas. By enforcing consistency of imaging and model derived motion, one or more material properties may be estimated using the modeling and scan data for a patient without intervention. An image-based automatic patient-specific model provides for automatic personalization of the valve biomechanical model by minimizing the Euclidean distances between model generated and image based mitral valve closure.

FIG. 1 shows a method for estimating a patient-specific material property of anatomy. The method is implemented by a medical diagnostic imaging system, a review station, a workstation, a computer, a PACS station, a server, combinations thereof, or other device for image processing medical data. For example, the system or computer readable media shown in FIG. 6 implements the method, but other systems may be used. A processor of any type of system, interacting with memory, user input, display, and/or other components, may perform the acts.

Figure 2:
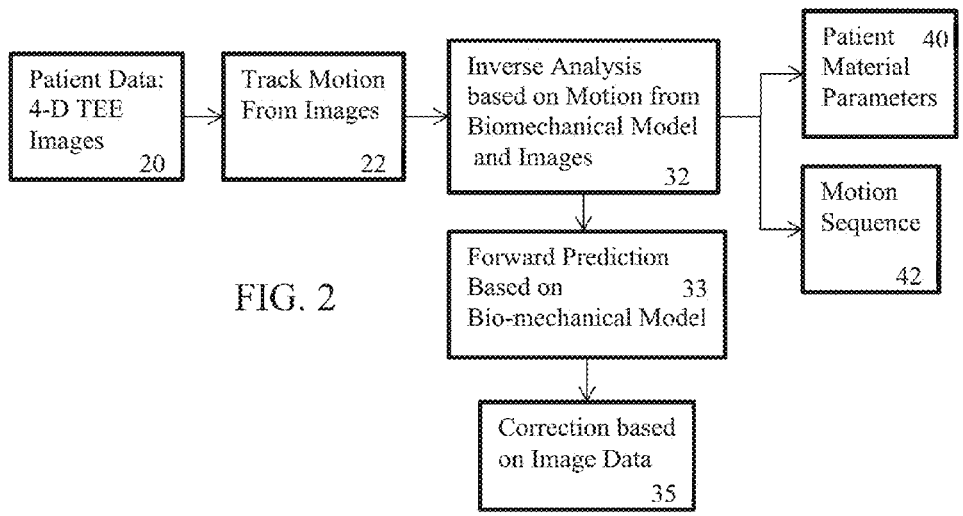

FIG. 2 shows another embodiment of the method for estimating a patient-specific material property. The method of FIG. 2 is similar to the method of FIG. 1, but highlights different aspects of the flow. For the method of FIG. 2, the patient-specific material parameters and physiologically significant motion from is estimated from 4-D TEE images 20. The proposed method is a two-step procedure: first, extract the mitral valve geometry sequence from the images in act 22, and then treat the motion sequence as an observation of the outcome of the mitral valve system in act 33 and perform inverse analysis in act 32 to fit in act 35 the image-based observation into the biomechanical model. An extended Kalman filter approach is used for the inverse analysis to produce a sequence of kinematics states 42 and material parameter estimates 40.

Figure 3:
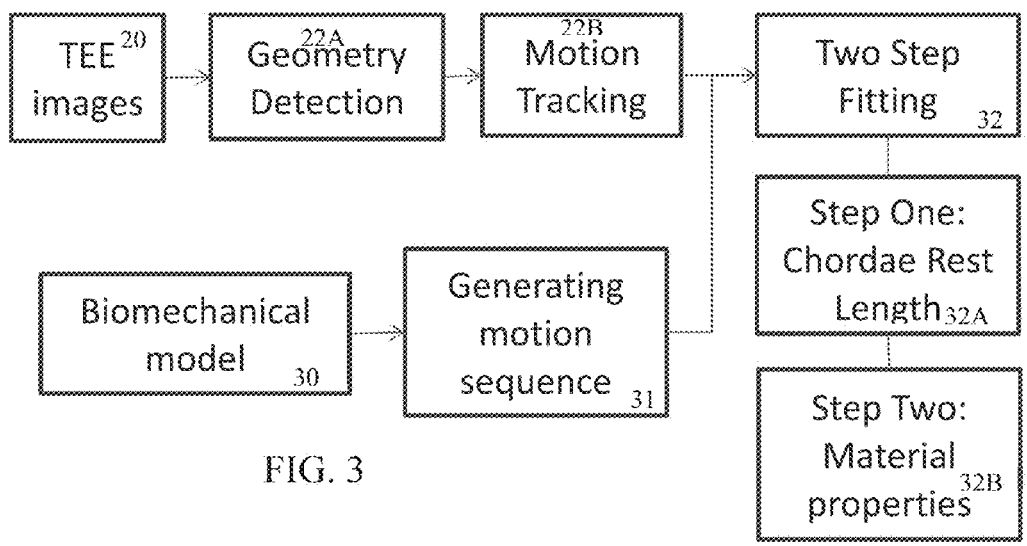

FIG. 3 shows yet another embodiment of the method for estimating the patient-specific material property. The method of FIG. 3 is similar to the methods of FIGS. 1 and 2, but highlights different aspects. The mitral valve closure process from the end diastole is studied, but the opening process may instead or additionally be studied. Diastole is the last frame ($I_0$) where the mitral valve is seen fully open in TEE images 20. The closure motion continues until the first systolic frame ($I_N$) where the mitral valve is seen maximally closed. The algorithm first estimates the leaflet geometry at the nth frame ($g_n$) in act 22A and tracks motion in act 22B to ensure inter- and intra-patient point correspondence of the geometric representation. Inter-point correspondence requires relationships among anatomy seen across patients. The intra-point correspondence requires relationships across time for a given patient. The biomechanical model 30 is used to generate a motion sequence ($h(g_0, m)$) in act 30. The biomechanically modeled motion is fit to the image-based observation by adjusting a set of patient-specific material parameters (m) of the biomechanical model in act 32. In one example, the material parameters are composed of leaflet biomechanical parameters (e.g., Young's modulus of different parts and the chordae rest length). The estimation problem is formulated as:

$$m = \min_m f(m) = \min_m |g_n - h(g_0, m)|$$

where the cost function is represented by the Euclidean distances between the biomechanical model generated and image observed mitral valve closure. The personalization is achieved by minimizing the cost function to obtain the patient-specific parameters. The cost function may be modified to penalize the mismatch in degree of coaptation for certain clinical applications when matching at the leaflet edge is more important than other regions. To solve the optimization problem, a two-step procedure is followed where chordae rest length is first solved in act 32A and then other material properties (e.g., Young's moduli of the leaflets) are solved in act 32B. The two procedures may be combined into one—solving for both at a same time. Other divisions or reverse order may be used.

The methods of FIGS. 1-3 are implemented in the order shown or a different order. Additional, different, or fewer acts may be performed. For example, the categorization and/or display of acts 36 and 38 of FIG. 1 are not performed. As another example, act 28 is not performed.

The acts may be performed in real-time, such as during scanning. The model may be parameterized or generated while scanning to acquire another dataset representing the volume. The acts may be performed during an appointment or off-line in a review period. The patient-specific data may be associated with previous acquisition rather than in real-time. Measurements and/or images of automatically detected anatomy may be provided in seconds, such as 10 or fewer seconds. Alternatively, the acts are performed as desired by a clinician regardless of whether a patient is currently at the facility or being scanned.

The acts may be performed automatically by a processor. The user causes the patient to be scanned or obtains scan data for the patient from a previous scan. The user may activate the process. Once activated, the anatomy is identified, and patient-specific values of one or more material properties are determined without further user input. User input of locations of the anatomy in any of the scan data may be avoided. Some user input may be provided, such as for changing modeling parameter values, correcting detected locations, and/or to confirm accuracy.

The models are based on scan data from a patient acquired in act 20 (see FIGS. 2 and 3). This patient-specific modeling may result in the anatomy locations and/or material properties being different for different patients. For one patient, the material property (e.g., chordae length and/or Young's modulus) may be different than an average or another patient. Since the modeling relies on the patient-specific scan data, patient specific properties may be determined.

For patient specific modeling, one or more sets of scan data are obtained. Ultrasound, magnetic resonance, or computed tomography data is obtained. In one embodiment, 4D computed tomography data is used as disclosed in U.S. Pat. No. 8,009,887. Any medical imaging modality capable of scanning a volume multiple times during a heart cycle may be used, such as TEE echocardiography. The ultrasound scan data corresponds to a data set interpolated to a regular 3D grid, displayed images (e.g., detected and scan converted ultrasound data), beamformed data, detected data, and/or scan converted data. Imaging data may be a frame or volume of data representing a volume. The imaging data may be data from the processing path derived before generating an image or data for a display as an image. A frame or volume of data may be data in an image format or data in a different format (e.g., scan format or representing a three-dimensional grid). The ultrasound data represents a volume or 3D region of a patient.

The volume region includes tissue, fluid, or other anatomy structures. Different structures or types of structures react to the acoustic energy differently. The shape of a structure or spatial aspect may be reflected in B-mode or harmonic data. The flow of fluid may be reflected in color flow, Doppler, spectral Doppler, or Doppler flow data.

In act 22, motion of the anatomy is derived from the scan data of the patient. For example, motion of the mitral valve is estimated. Locations for different parts of the valve are calculated. The locations for anterior and posterior papillary tips, mitral annulus, and anterior and posterior leaflets are estimated (act 22A). A mesh representing the valve is estimated. The papillary heads may be located for chordae. Additional, different, or fewer anatomic locations may be used, such as the papillary tips. For patient-specific estimation, the locations of the anatomy are estimated using medical diagnostic data of the patient. The medical diagnostic data may be scan data, such as image data. Image data is used to include scan data or data to be processed into an image as well as data of a displayed image. Data representing the valve or volume of the heart is used for determining the locations of the anatomy. For estimating from the model relative to a particular patient, patient-specific aortic-mitral model estimation is provided from patient-specific scan data.

The processor estimates an anatomy model of the valve of a patient from the medical diagnostic imaging data of the patient. The estimation is data-driven. For determining the location, shape, motion, size or other characteristic of a heart valve, the valve is modeled generally. The model is fit to patient specific data by estimation. Any estimation may be used, such as disclosed in U.S. Published Patent Application No. 2010/0240996, the disclosure of which is incorporated by reference. The estimation is performed in sequential stages, such as associated with a hierarchal model. For example, a location of the global valve relative to the heart volume is estimated, one or more locations in the valve relative to other portions of the valve are then estimated, and then a surface of the valve is estimated. Each stage may use the same or different algorithms. For example, separate machine-learnt algorithms are used for each stage. Different models may be estimated from the frames of data for different stage, phase, or type of anatomy.

In one embodiment, a physiological model of the aortic and mitral valves is designed to capture complex morphological, dynamical, and pathological variations. The hierarchical definition is constructed on three abstraction levels: global location and rigid motion model, non-rigid landmark motion model, and comprehensive aortic-mitral model. Along with the parameterization, an anatomically driven re-sampling method to establish point correspondence required for the construction of a statistical shape model is provided. A collision detection and repair algorithm may provide physiological consistency.

To capture a broad spectrum of morphological variations, the model is parameterized by three coarse-to-fine components: i) three transformations B for global location, orientation and scale over the cardiac cycle; ii) the trajectories of ten anatomical landmarks $L(B)=(l1 \ldots l10) \in R^{3 \times 10}$ (e.g., two trigones, one posterior annulus mid-point, two commissures, two leaflet tips and three papillary tips); and iii) a triangulated surface mesh $S_{LA}(B, L)$ to represent the left atrial (LA) surface of both anterior and posterior leaflets. The positions of the vertices of the LA surface are constrained by the anatomical landmarks, resulting in an anatomically consistent parameterization that ensures intra- and inter-patient point correspondence.

Other meshes may be used, such as tetrahedral mesh. The estimated mesh represents the valve. The mesh represents a surface of the valve. Different surfaces, S, are determined for the different times or phases of the heart cycle. In one embodiment, the surfaces, S, are each a point distribution model of 986 points and 1792 triangles with consistent parameterization derived from anatomical landmarks (three trigones, three commissures, two leaflet tips and three papillary heads). Other numbers of vertices and/or triangles may be used.

Since it is still difficult to measure the thickness of the leaflets reliably, the thickness is set to a value, such as 2 mm (e.g., an average measure for all patients). In one example, the one layer leaflet surface mesh is extruded towards the ventricle for a set distance, which is 1.32 mm and 1.26 mm for the anterior and posterior leaflet, respectively, thus forming a volumetric structure. The single layer mesh of the leaflets is shifted towards the left ventricle in the direction of the surface normal to construct the volumetric structure. Next, the volumetric structure is discretized into tetrahedral meshes. The tetrahedral mesh is generated from this volumetric structure for the biomechanical model.

Any model may be used. In one embodiment, the estimation is a function of a discriminative probabilistic model in act 28. The model detects the locations of anatomy based on probability. The location associated with a highest probability, after any weighting or other consideration, is selected as the location for the anatomy. Different locations have different probabilities for representing the anatomy of interest. One type of discriminative probabilistic model is a machine-learned model. Other models may be used.

Combinations of different types of models may be used for the anatomy model. For example, different detectors are employed for the mitral annulus and free-edges contours and the leaflet surfaces to improve detection accuracy.

The anatomy model is estimated from the patient specific data. The patient specific data is an input feature to the model, such as a machine-learned matrix. In one embodiment, B, L(B) and $S_{LA}(L, B)$ are estimated from the frames of data using a hierarchical discriminative learning algorithm. The probability p(B, L, S|I), given the frame of data I, is incrementally modeled within the Marginal Space Learning (MSL) framework, based on the Probabilistic Boosting Tree (PBT). Given a test image, the MLS framework finds position candidates around the MV based on Haar and/or steerable features. The position candidates are then successively refined by rotation and scaling candidates. This defines a region of interest inside which the positions of ten landmarks are estimated using the same strategy.

In one embodiment, a robust learning-based algorithm, which in concordance with the hierarchical parameterization, includes three stages: global location and rigid motion estimation, non-rigid landmark motion estimation and comprehensive aortic-mitral estimation. Each stage may be implemented differently. In one embodiment, trajectory spectrum learning (TSL) with local-spatio-temporal (LST) features is used for the non-rigid landmark motion estimate. The number of stages may be fewer or more. The same algorithm is used for either ultrasound or computer tomography data. Alternatively, different algorithms are trained for the different types of data.

Any machine training may be used for one or more stages. The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

The classifier is trained from a training data set using a computer. Any number of expert annotated sets of data is used. For example, about 200 hundred volume sequences representing the heart and including one or more valves are annotated. The annotation indicates valve landmarks and/or surfaces within the volumes. The different anatomies of each volume are annotated. This large number of annotations allows use of a probabilistic boosting tree to learn relevant features over a large pool of 3-D Haar, and/or steerable features. Both features may be efficiently computed and be effective as a feature space for boosting classifiers. Other features may be used. Each classifier uses the data sets and annotations specific to the anatomy being classified.

In one embodiment, the classifier is a knowledge-based probabilistic model, such as marginal space learning using a hierarchical search. A database of known cases is collected for machine learning, providing a database-driven knowledge-based approach. For training data, three-dimensional context information is preserved and guides the detection process. Training and detecting the location of measurement indicators include detecting the associated anatomy since the measurement indicator indicates the anatomy. The classifier learns various feature vectors for distinguishing between a desired anatomy and information not being detected. In alternative embodiments, the classifier is manually programmed.

For learning-based approaches, the classifier is taught to distinguish based on features. For example, the probability model algorithm selectively combines features into a strong committee of weak learners based on Haar-like local rectangle filters whose rapid computation is enabled by the use of an integral image. Features that are relevant to the anatomies are extracted and learned in a machine algorithm based on the experts' annotations, resulting in a probabilistic model. A large pool of features may be extracted. The training determines the most determinative features for a given classification and discards non-determinative features. Different combinations of features may be used for detecting different anatomies, the same anatomy at different resolutions, and/or the same anatomy associated with different translation, rotation, or scale. For example, different sequential classification stages utilize different features computed from the 3D volume data. Each classifier selects a set of discriminative features that are used to distinguish the positive target from negatives. The features are selected from a large pool of features. The large pool is determined by a programmer or may include features systematically determined.

A tree structure may be learned and may offer efficiency in both training and application. In the midst of boosting a multi-class classifier, one class (or several classes) may have been completely separated from the remaining ones and further boosting yields no additional improvement in terms of the classification accuracy. For efficient training, a tree structure is trained. To take advantage of this fact, a tree structure is trained by focusing on the remaining classes to improve learning efficiency. Posterior probabilities or known distributions may be computed, such as by correlating anterior probabilities together.

To handle the background classes with many examples, a cascade training procedure may be used. A cascade of boosted binary-class strong classifiers may result. The cascade of classifiers provides a unified algorithm able to detect and classify multiple objects while rejecting the background classes. The cascade structure corresponds to a degenerate decision tree. Such a scenario presents an unbalanced nature of data samples. The background class has voluminous samples because all data points not belonging to the object classes belong to the background class. Alternatively, the classifiers are sequentially trained without cascade.

The probabilistic boosting tree (PBT) unifies classification, recognition, and clustering into one treatment. A probabilistic boosting tree is learned for each anatomy or stage of interest. The classifier is a tree-based structure with which the posterior probabilities of the presence of the anatomy of interest are calculated from given data. Each detector not only provides a binary decision for a given sample, but also a confidence value associated with the decision. The nodes in the tree are constructed by a combination of simple classifiers using boosting techniques.

By inputting the patient-specific data, the anatomy model is estimated for a given patient. The locations for the anatomy are estimated for a given time, such as end-diastole, and/or for a sequence of times, such as throughout a heart cycle. The anatomy model may include input information not obtained from the scan data.

Figure 4:
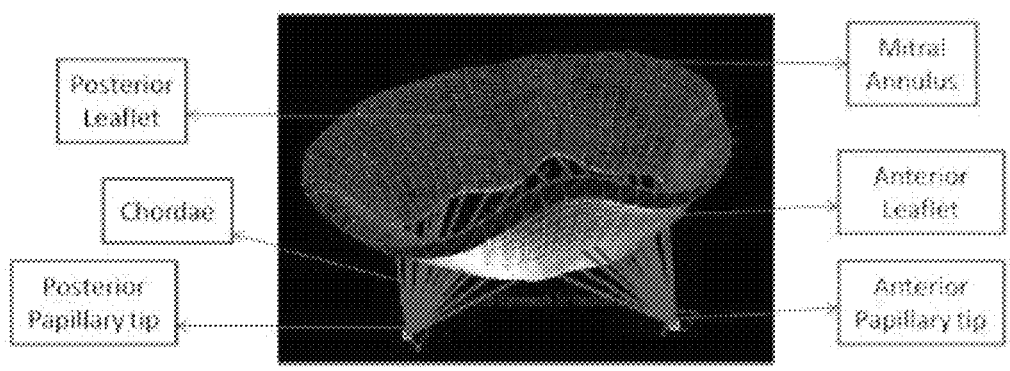
FIG. 4 is an illustration of example landmarks and mesh for a heart valve.

The anatomy model may include a mesh fit to the valve based on the detected anatomy (see FIG. 4). The model outputs the mesh or the mesh is formed based on the locations of anatomy output by the model. The point-distribution model of the MV surface is mapped according to the landmarks and deformed, within the learned space of shapes, according to boundary detectors estimated through PBT.

The same or different model or group of models is used for the initial identification of anatomy locations. For example, the locations are detected in a first iteration or in preparation for a first iteration. For later iterations, the locations (e.g., surface, area, line, or point) are refined. The model may accept as input the frame of scan data and/or the surface. In one embodiment, the surface position is refined by using a previously detected surface and the patient-specific data as inputs to the model. The refining uses a machine-learned matrix of a discriminative probabilistic model. The initial detection uses the same or different machine-learned matrix.

The mitral annulus and papillary tips motion are also quantified from the images to be used as prescribed information in the biomechanical model. The marginal and basal chordae are attached between papillary head and leaflet free edges. The insertion points are determined by visual inspection, such as based on user input relative to an image. The complete mitral valve geometry is shown in FIG. 4, and the blue trajectories indicate the mitral annulus and papillary tips motion. The morphological model represents a volumetric structure, including fiber orientation and modeling of the chordae.

The locations for the same anatomy at different times are found in act 26. The same or different model is used for detecting the anatomy at different phases. The method may be performed for two frames representing different times. The heart cycle is cyclical, so has phases. Example phases are diastole and systole. The method is performed on two frames of data from different times and representing different phases of the heart cycle. For example, one frame represents diastole and the other frame represents the heart volume 0.05-0.3 seconds later.

The method may be applied on the entire 4D time series of frames, such as performing the method for a moving window of pairs of frames throughout the cycle. Any number of frames for a given cycle and corresponding phases may be used, such as 2-40. The frames representing different phases may be acquired from different cycles, but are temporally positioned to represent the heart over a cycle.

The description below is for two frames $I_{t1}$ and $I_{t2}$ at times t1 and t2 only, for the sake of clarity.

The estimation is performed for each of the frames of data or different times as represented by act 22A. Since each frame is for a different phase, the estimates are of the locations of the anatomy at different times. The model parameters are estimated from volumetric sequences (3D+time data) to construct patient-specific aortic-mitral representations. For different times, independent estimation is used, or the determined locations are tracked in act 22B, such as using correlation or other tracking. The estimation for the different frames may initially be independent of estimation for other frames. For later iterations, the estimation for any given frame may be based, at least in part, on the estimated locations of the anatomy in frames representing other phases. The MV anatomy is tracked in act 22B over the cardiac sequence using a manifold-based motion model.

In act 30, the anatomy, such as the mitral valve, is modeled with a biomechanical model. The biomechanical model incorporates material properties rather than just the dynamic behavior of the morphological model.

To personalize the biomechanical model, the geometry or location information at a given phase or different phases may be incorporated into the biomechanical model. For example, the geometry at the end diastole is then further processed to be loaded into the biomechanical model. The mitral annulus motion and the papillary tip motion (e.g., trajectories or displacement) derived from the TEE images may be used as a boundary condition for the biomechanical model.

Fiber models are mapped on the leaflets where the fiber directions are mainly parallel to the annulus while those in the anterior leaflet close to the commissures gradually rotate to become perpendicular to the annulus. The chordae are attached between the leaflet and the papillary tips, such as determining the attachments for twenty eight marginal chordae and eight basal chordae. The insertion points are determined by visual inspection and are identical for all the patients. Automatic placement of the insertion points may be provided. The geometry at early systole may be processed in a similar manner and used in the automatic personalization process.

The anatomy locations from different times are used as a starting point for the biomechanical model. The biomechanical model relates the physical mechanics of the valve from one time to another time. Based on the physics or physical structure, the biomechanical model is applied to determine the change in the anatomical locations over time to the given time.

For a pair of frames (e.g., closure and open), a converse alteration is performed. For time one, the locations from time two are used as the starting point for the biomechanical transform to time one. For time two, the locations from time one are used as the starting point for the biomechanical transform to time two.

The deformations between times are calculated by solution of a dynamic system. The dynamic system represents the change due to physical operation of the valve. For example, the dynamic system includes terms for mass, damping, stiffness, displacement, velocity, and acceleration. Additional, different, or fewer terms may be used to represent the operation of the valve.

In one embodiment, the dynamic system of the biomechanical model is represented as:

$$M\ddot{U}+C\dot{U}+KU=F_{ext}$$

where U is the displacement vector of the vertices of the mesh, $\dot{U}$ is the velocity of the vertices, and $\ddot{U}$ is the acceleration of the vertices, M is a diagonal mass matrix (e.g., leaflet mass density $\rho$=1.04 g/mL), C is a Rayleigh damping matrix (e.g., C=0.1(M+K)), and K is the stiffness matrix of the internal elastic forces. The tissue properties of the leaflets are represented as a linear isotropic material to optimize computational efficiency for fast estimation. The leaflet thickness is set to 2 mm or other value since imaging may not accurately represent this thickness. If the thickness information is available from imaging data, then the measured thickness may be used. The thickness is an average from representative patients, but other thicknesses may be used. Alternatively, leaflet thickness is solved for as a patient-specific material property. Near-incompressibility is achieved with a Poisson ratio v of 0.488 and a Young modulus E of 6.2 MPa. Alternatively, the Young's modulus and/or the Poisson ratio are solved as patient-specific material properties. Other dynamic representations of the biomechanical model may be used.

The leaflets are modeled as linear, transverse isotropic elastic tissues. The leaflets may behave as linear materials in the range of physiological pressures even if modeled throughout the cycle. Linear elasticity models are also computationally efficient, allowing fast simulations and real-time intervention planning. Any linear relationship may be used for basal and marginal regions, such as an initial generally inelastic region followed by a linear increase in elasticity as a function of force. In alternative embodiments, the curved lines or other representation of the leaflet tissue is used. The proposed method may also be applied if a non-linear model for leaflet mechanics in used in place of the linear model.

Different or the same tissue properties are assigned to the AL and PL, such as AL Young's modulus of $E_{ALf}$=6.233 MPa, $E_{ALf}\perp$=2.350 MPa, AL shear modulus of $G_{ff}\perp$=1.369 MPa, PL Young's modulus of $E_{PLf}$=2.087 MPa, $E_{PLf}\perp$=1.887 MPa, and PL shear modulus of $G_{ff}\perp$=0.694 MPa. Other values representing the tissue may be used. Alternatively, one or more region specific tissue properties are solved as patient-specific material properties.

In the dynamic system, the force, $F_{ext}$, applied for solving the biomechanical model emulates a spring. Other forces may be added or used instead of a spring force. The force is directional, such as at a normal to the anatomical location. The normal is at the surface for each location, such as at each vertex. Force at other directions may be used.

The force may be weighted. For example, the force is weighted by an amount of altering. Greater alterations may result in greater force. A difference in velocity, position, or acceleration of vertices from different times is used as the weight. The inverse relationship may be used. Other or no weighting may be used.

The force is calculated from the surface or other anatomy locations at one time for alteration of the anatomy locations for a different time. The surface for the one time is deformed based on the biomechanical model of the valve with the external force calculated from the surface used as the starting point. $F_{ext}$ is the external force that drives a location at one time towards the new estimate of the location. To make the result as close as possible while preserving the tangential motion generated by the internal forces, the vertices are moved long their normal direction n, towards their corresponding vertices at another time. In one embodiment, the force is weighted according to the uncertainty in the data term $\rho(v_{t1}|I_{t1})$ such that positions with low confidences have little influence on the leaflet deformation, while high confidences result in high influence. For example, $F_{ext}$ is written as:

$$F_{ext}(v_{t2}") = -\kappa \rho(v_{t1}'|I_{t1})(v_{t1}'-v_{t2}")\cdot n$$

where $\kappa$ is a weight parameter. Any value may be used, such as empirically setting $\kappa$ to 0.1.

In another embodiment, $F_{ext}$ is the total force developed by the chordae, $F_c$, and heart pressure, $F_p$. A generic profile that increases from 0 mmHg to 120 mmHg is used for the heart pressure. The force exerted by chordae is related to the material property, morphology, and elongation of the chordae, and may be solved for as patient-specific material properties or may be based on a generic representation. The force, $F_c$, induced by the chordae is calculated using the following equation: $Fc(v_i, p_i, t) = -k_{c,i}(\epsilon_{c,i}, t) \times (L_i(t) - L_{i,0})$ where $L_i(t)$ is the current elongation, $L_{i,0}$ is the chordae rest length, $\epsilon_{c,i}(t) = (L_i(t) - L_{i,0})/L_{i,0}$ is the strain, $k_{c,i}$ is the spring tensile stiffness and related to chordae material properties. Other force equations may be used.

For calculating motion, the biomechanical model is solved as a finite element model. The various components are spatially and temporally handled in discrete steps. The dynamics are solved as a linear system using acceleration, velocity and position.

In one embodiment, the vertices $v_{t2}"$, and thus the force, $F_{ext}$, are updated at every time step of the resolution of the dynamic system. The equation is solved using co-rotational triangular finite element methods (FEM) to cope with large deformations and rotations of the anatomy of the valve. An implicit Euler solver is employed to update mesh positions. The deformation ends when the average relative displacement of the surface vertices is lower than the image resolution (typically 1 mm). This solution is performed for each iteration.

The finite element modeling is performed without user input of anatomy locations. The user may activate the creation of models and simulation, but input of locations of anatomy is avoided. The simulation is performed automatically. In alternative embodiments, the user confirms or indicates locations of anatomy for creation of models or control of the closure simulation. For example, the user inputs chordae locations or insertion points.

The biomechanical model is a function of the motion and one or more patient-specific material parameters. For example, the Young's modulus, chordae rest length and/or other material parameters or other mechanical property are accounted for in the biomechanical model. One or more of these material properties may be solved for a patient-specific value. Other material properties may be assigned or predetermined, whether by measurement or by using a generalized or generic (e.g., average) value.

Since chordae may be difficult to visualize, chordae may be solved for patient-specific values. Chordae rest length may have a significant influence on the motion predicted by the biomechanical model. In one embodiment, 28 marginal chordae and 8 basal chordae are included in the biomechanical model as patient-specific material properties. The chordae may be divided in four groups based on the leaflet and papillary tip to which the chordae are attached.

Alternatively or additionally, Young's modulus is included as a patient-specific material property. The mitral leaflets are modeled as linear, transversely isotropic and nearly incompressible elastic tissues. The tissue material properties, including Young's modulus along and across the collagen fiber and shear modulus ($E_{ALf}$, $E_{ALf}\perp$, $G_{AL}$, $E_{PLf}$, $E_{PLf}\perp$, and $G_{PL}$, respectively) of the anterior and posterior leaflet are assumed to be different for different patients.

In one embodiment, the target set of patient-specific parameters are defined as $m=[E_{ALf}, E_{ALf}\perp, G_{AL}, E_{PLf}, E_{PLf}\perp, G_{PL}, L_{1MA}\text{-}L_{14MA}, L_{1MP}\text{-}L_{14MP}, L_{1BA}\text{-}L_{4BA},$ and $L_{1BP}\text{-}L_{14BP}]$ where $L_{MA}, L_{MP}, L_{BA},$ and $L_{BP}$ are the chordae rest length of the marginal and basal chordae attached to anterior and posterior papillary tips. Only one, different, or additional patient-specific parameters may be used. Other material characteristics may be included. For example, more than one stiffness measure may be used for each chordae. The stiffness along a chordae may be different than the stiffness in a perpendicular direction. The other material parameters of the biomechanical model use non-patient-specific values.

Given values for the various material properties, the displacement from the morphological model (e.g., displacement measured from scan data), and any boundary conditions from the scan data, the biomechanical model may be used to estimate motion of the anatomy. Force is applied and the resulting motion of the modeled anatomy is determined. For a first iteration, default values may be used for the patient-specific material properties. The default values may be population based. Using the biomechanical model, the motion from one time to another (e.g., from end diastole to end systole) is determined for various locations, such as the mesh and other parts of the anatomy. The displacement or the end locations represent the motion.

In act 32, the patient-specific mechanical or material properties are solved for inversely. As part of the inverse solution, a forward projection of the motion using the biomechanical model is calculated in act 33. The forward projection uses values of the patient-specific properties, such as default or later refined values. The resulting biomechanically predicted motion is compared in act 35 to the morphologically modeled (e.g., motion from the scan data) motion. Motion may be compared in terms of a magnitude and direction of change, difference in positions, or position resulting from the motion. The comparison provides an indication of accuracy of the current patient-specific material properties. If converged or sufficiently resolved, the difference in motion for all or a sub-set of anatomy locations is below a threshold.

If above the threshold for any one or other number of locations, the solution is not converged. Other values of one or more patient-specific material properties are used. The changes may be altered sequentially, such as solving for one patient-specific material property and then another, or may be performed in parallel, such as solving for multiple values in each iteration.

The amount and/or direction of the change in values may be determined in an iterative solution. Any optimization or minimization may be used. In one embodiment, the non-linear function of the biomechanical function is solved with an extended Kalman filter. In other embodiments, other filtering with or without noise terms is used. In yet other embodiments, gradient descent or other optimization or minimization algorithms may be used. Non-gradient approaches may also be used. Any cost function may be used in the optimization problem.

By iteratively repeating the calculation of the motion with the biomechanical model using updated values for the patient-specific material properties and the comparison of the output motion with the detected motion from the patient, the values that result in the biomechanical model performing as indicated by the morphological model (i.e., detected motion) are found.

For the inverse solution, the dynamic equilibrium equation (i.e., biomechanical model) is transformed into state space representation of the system, provided by:

$$x_k = f(x_{k-1}) + w_{k-1} = x_{k-1} + w_{k-1}$$

$$y_k = h(x_k) + v_k$$

where $x_k$ is the material parameter vector at the kth image frame, which stays constant during the cardiac cycle, $y_k$ is the position of the mitral leaflet at the kth image frame, which is calculated by adding the reference position and displacement U, and $w_{k-1}$ and $v_k$ are the process and observation noises, respectively. Other representations may be used, such as without the noise variables. The displacement vector $U = K^{-1}(F - M\ddot{U} + C\dot{U})$ is a non-linear function of the material parameters, so the location $h(x_k)$ is also a non-linear function of $x_k$. To solve the system, an extended Kalman filter (EKF) adopts a prediction-correction process in the estimation. The material property of the mitral valve is identified by the recursive filtering procedure as following:

Initialization:

$$x_0 = \mu, P_0 = P_0 \qquad (4)$$

Prediction:

$$x_k^f \approx f(x_{k-1}^a) \qquad (5)$$

$$P_k^f \approx J_f(x_{k-1}^a) P_{k-1} J_f^T(x_{k-1}^a) + Q_{k-1} = P_{k-1} + Q_{k-1} \qquad (6)$$

Kalman gain:

$$K_k = P_k^f J_h^T(x_k^f) J_h(x_k^f) P_k^f J_h^T(x_k^f) + R_k)^{-1} \qquad (7)$$

Correction:

$$x_k^a = x_k^f + K_k(y_k - h(x_k^f)) \qquad (8)$$

$$P_k = (1 - K_k J_k((x_k^f)) P_k^f \qquad (9)$$

where $J_f$ is the Jacobian matrix of f and an identical matrix I in this case, and $J_h$ is the Jacobian matrix. $h_i(x_k)$ is the position of ith element, and $\Delta x_{j,k}$ is the finite increment of the jth component of vector $x_k$. The formulation keeps the finite element method as an independent module and uses the output of the finite element method for the calculation of the Jocaobian matrix for Kalman filtering.

In one example embodiment, the inverse solution is used to solve for a plurality of mechanical properties, m, of the valve of the patient. The goal of personalization is to determine a set of parameters that minimizes the distance (f(m)) between the biomechanical model driven and the image-observed mitral valve closure. In this example, the chordae rest length and Young's modulus are solved sequentially in acts 32A and 32B. The first step aims to personalize the rest length using a coarse-to-fine maximum derivative method. This method may be represented as an example algorithm:

Algorithm 1 Coarse-to-fine maximum derivative
1. Initialize the chordae rest length using the point-to-point distance from the papillary tip and the insertion points at the end systole;
2. At Jth level, change the group of the parameters in the direction of maximum derivative to reduce the cost function;
3. Repeat 2 until the cost function does not change between two consecutive iterations
4. Go to the (J+1)th level and repeat 2, 3

Twenty-eight marginal chordae are used, fourteen attached to each leaflet and seven attached to each papillary tip. Eight basal chordae are used, four attached to each leaflet and two attached to each papillary tip. Fixing the material parameters, thirty-six parameters are to be estimated in the first step (m1=[$L_{1MA}$-$L_{14MA}$, $L_{1MP}$-$L_{14MP}$, $L_{1BA}$-$L_{4BA}$, $L_{1BP}$-$L_{4BP}$]). There are four levels from coarse-to-fine for the biomechanical models, but other numbers of levels and/or chordae may be used. Eight groups of the parameters are used in the first level following the chordae location where seven marginal chordae form one group, while two basal chordae form one group. The grouping becomes finer in each level. Seven groups of marginal chordae and eight groups of basal chordae are used in the second level. Fourteen groups of marginal chordae are used in the third level, and each of the marginal chordae rest length is estimated individually in the fourth level. Using coarse-to-fine solution provides better computational efficiency since the optimization at the coarse level provides a better starting point for finer tuning.

The second step of the algorithm aims to personalize material parameters using the extend Kalman filter (EKF) approach since EKF provides a stable sequential least square solution and may be efficient for material parameter estimation. Once the chordae rest length is fixed or solved, there are six parameters (m2=[$E_{ALf}$ $E_{ALf}\perp$, $G_{AL}$, $E_{PLf}$, $E_{PLf}\perp$]) to be estimated, four of which may be derived from the other two. The ratio of Young's modulus along and across the fiber (r=$E_f$/$E_f\perp$) is fixed or solved and the shear modulus is approximated by G≈Ef/2((1+v))) to ensure the physiological consistency of the parameters. The state space representation is written as follows:

$$m_{2,k} = f(m_{2,k-1}) + w_{k-1} = m_{2,k-1} + w_{k-1}$$

$$g_k = h(m_{2,k}) + v_k$$

where $w_{k-1}$ and $v_k$ are the state and process noises, respectively, and assumed to follow Gaussian distributions with covariance matrix $Q_k$ and $R_k$, but other distributions may be used. The observation vector gk=[$x_{k1}$, $y_{k1}$, $z_{k1}$, ... $x_{ki}$, $y_{ki}$, $z_{ki}$, ... $x_{kL}$, $y_{kL}$, $z_{kL}$] is the geometry vector, which is represented by L number of vertices (e.g., L=3248 but another number may be used). The process function f(•) is derived from the assumption that material parameters and the chordae rest length stay constant during the cardiac cycle. The observation function h(•) is derived from the biomechanical model specifying loading, geometry, tissue property, boundary condition, and dynamic equilibrium function and is the same as in the cost function (e.g., represented by Euclidean distances).

The EKF estimation is first initialized with the general material parameters ($m\bar{}_{2,0}$,) and its covariance matrix (e.g., $Q_0$ equals the identity matrix) and then follows a prediction-correction iteration. In the prediction step, the targeted parameters $m^f_{2,k}$ are predicted to be the same as the last estimates. In the correction step, the predicted closure h($m^f_{2,k}$) using the predicted parameters $m^f_{2,k}$ is compared to the observation $g_k$ to generate new estimates $m^a_{2,k}$. The iterative process is stopped when the average distances of the locations of the patient-specific model and the locations of the image based estimation between two consecutive iterations are less than 0.01 mm or the maximum number of iteration is reached. The whole set of patient-specific parameters is obtained after the second step.

Using the inverse solution and the comparison of motion, the material properties, such as Young's modulus and/or rest length of at least two chordae, may be estimated for a patient in vivo. Scan data of the patient, without invasive measurements, is used to determine the material properties. Similarly, external force is not applied to the anatomy to determine the properties. A shear or longitudinal wave for elasticity imaging is not needed, so an acoustic force pushing pulse is not transmitted. Comparison of motion, such as displacements or positions resulting from displacement, between the observed and the biomechanical model, is used to find the properties.

In one embodiment, other information in addition to the biomechanical model is used. The solution of the patient-specific material properties also incorporates blood flow or other information. For example, the solution is a function of a Computational Fluid Dynamics (CFD) or a Fluid-Structure Interaction (FSI) model incorporating the biomechanical model. Invasive or non-invasively determined pressure, and/or flow measurements (Ultrasound Doppler, or Phase contrast MRI), or other source of fluid dynamics is included in the fluid-structure model, such as disclosed in U.S. Pat. No. 8,224,640. One or more aspects of the fluid dynamics may be solved in a patient-specific manner, such as solving for a pressure with the fluid-structure interaction model. Other or all fluid aspects may instead be used as observed information for matching in the solution or used as information for determining the material properties.

The material properties may be used in various ways. For example, the material properties are used in the biomechanical model to predict response to surgical intervention (e.g., performing a virtual surgery on the personalized model of the patient's anatomy) or for diagnosis from operation indicated by the biomechanical model. In act 36, one or more the patient-specific material properties are used to categorize a condition of the valve of the patient. The value of the material property is compared to a pre-determined value, such as an expected value. Tissue properties may be compared with a database of normal/abnormal tissue properties for patient stratification and/or diagnosis. For example, an abnormally high or low value may indicate a disease state for the valve. The tissue properties may be used for surgical and/or intervention planning. For example, the value of the material property may indicate whether surgical intervention is appropriate, in what way to intervene (e.g., minimally invasive, open surgery, or transcatheter), and/or an optimal approach for a given intervention.

Figure 5:
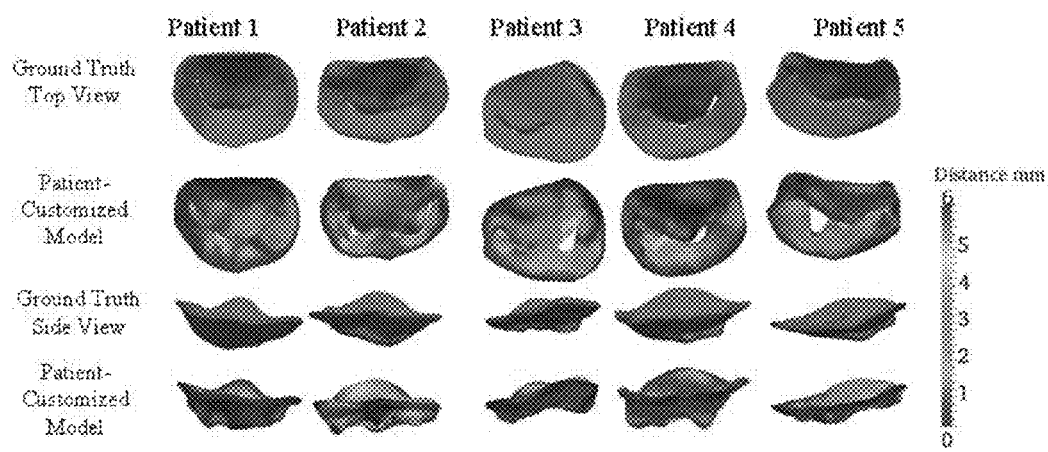
FIG. 5 illustrates example results of modeling heart valves.

In act 38, an image is displayed. The image is a function of the patient-specific value or values of one or more material properties. The value of the material property may be displayed, such as text or numbers in a list. In one embodiment, a position or sequence of positions (e.g., motion) of a model of the valve is displayed. The biomechanical model and corresponding mesh is used to generate an image. FIG. 5 shows examples of valve images for different patients from two different views. The biomechanical model uses the patient specific mechanical properties.

For imaging, an image of the valve is generated. The image is from the acquired scan data and/or from the biomechanical model. For example, the mesh representing the valve may be used for imaging. The image is a rendering of a three-dimensional volume. Voxels or data representing three-dimensional locations are rendered to a two-dimensional view. Ray casting, projection, surface or other rendering may be used. Two-dimensional planes may be alternatively be used.

In one embodiment, the surface is overlaid on a rendering of the heart or valves. The valve images are rendered from medical data with a same scale and perspective as an outline overlaid on the rendering. Color coding or other display modulation may be used with or in addition to an overlay. For example, different surfaces of the valve are rendered from B-mode data in gray scale with color modulation specific to the simulated surface. One surface may be rendered in one color and another in another color where brightness or shade is based on the material property.

One rendering or multiple renderings from the same volume may be displayed. In one embodiment, a sequence of images is displayed. The sequence is rendered from the different volumes throughout a portion (e.g., simulating closure) of or the entire heart cycle. For each image in the sequence, the corresponding detected or estimated valve information is displayed. The surface corresponding to the valve at the given time represented by an image is displayed. The images of the sequence may be displayed in succession to show or represent the motion of the valve. The representation of the valve is generated as a function of the surfaces simulated through the sequence.

In another embodiment, the tissue properties themselves are visualized. Some aspect of the image, such as color, shade, and/or brightness, is modulated as a function of the patient-specific values of the material properties. For example, the scan data is used to generate a three-dimensional rendering of the valve over time. The pixels for different regions of the valve are displayed with a color set based on the patient specific values. Any type of image of the valve may be generated, such as a polar plot or regional distribution image.

The displacement or motion used may be from opening to closure or closure to opening. Data for only two times is needed. In other embodiments, greater temporal resolution is used, such as using motion for three or more different times from closure to opening or opening to closure. The additional comparisons may lead to more accurate estimates of the material properties. Motion over a greater or lesser extent of time may be used, such as motion over an entire heart cycle. Different temporal windows or ranges of motion may be used to separately estimate the material properties. These separate estimates may be averaged or used separately for the biomechanical model for different phases of the cardiac cycle.

From the 4D anatomical or biomechanical model of the MV as constrained by the dynamic system, different metrics may be calculated. The dynamic change of the anterior-posterior (AP) annular diameter, computed as the difference diameter between early systole and early diastole, may discriminate the normal patients from functional mitral regurgitation patients. The change in diameter may indicate a reduced accentuation of the saddle shape with consequent reduction in leaflet coaptation. In addition to a dilated, akinetic annulus, the anterior surface length may be larger for patients with functional mitral regurgitation. The choice of ring size and type may be based on these automated measurements. Automated 3D quantitative surgical anatomy in FMR shows that an akinetic annulus is an early basis for MR, followed by annular dilatation and anterior leaflet lengthening, and that these mechanistic insights and the quantitative characterization of the pathological anatomy may aid surgical decision-making.

In one test, the method above is evaluated on datasets of simulated dynamic motion. The mitral valve geometry at an open state is used to generate the motion sequence. The material parameters are known when generating the motion sequence so the estimated material parameters may be compared to the ground truth. The material property is assumed to be homogeneous within the anterior and posterior leaflets but regionally different. Only two frames including the open and closed mitral valves are used to perform the parameter estimation since the closing state is the most important morphology when evaluating the mitral valve disease, such as mitral stenosis and regurgitation. Both the material parameters (Young's modulus in anterior and posterior leaflet, EA and EP) estimates and the refined closing state geometry to the simulated data, which is noise free, are compared to the ground truth. The results are shown in Table 1 where the point-to-mesh distance is the Hausdorf distance between two meshes.

TABLE 1

|  | s1 | s2 | s3 |
| --- | --- | --- | --- |
| EA True (MPa) | 6.2330 | 5.7880 | 6.2330 |
| EP True (MPa) | 6.2330 | 5.7880 | 4.3631 |
| EA Estimate (MPa) | 6.2714 | 5.8653 | 6.2101 |
| EP Estimate (MPa) | 6.2714 | 5.8653 | 4.6570 |
| Estimation error (%) | 0.62 | 1.27 | 3.55 ± 4.51 |
| Point-to-mesh distance (mm) | 0.0678 ± 0.0613 | 0.2030 ± 0.1864 | 0.0712 ± 0.0588 |

|  | P1 |
| --- | --- |
| EA (MPa) | 7.8047 |
| EP (MPa) | 3.2530 |

The results demonstrate that the method accurately estimates the material parameters with less than 5% error and the refined motion with less than 1 mm point-to-mesh distance.

The proposed method is also tested on sets of patients' TEE images. Similarly, the geometry at open and closed state is used as the observation to perform the inverse analysis. It is difficult to validate the real material property for each patient since there is no direct measurement. So, the similar trend in the anterior and posterior parameters for normal patients is used to indicate validity.

|  | General (mm) | Personalized (mm) |
| --- | --- | --- |
| P1 | 2.4018 ± 1.0089 | 2.2280 ± 0.9200 |

In another verification, the automatic personalization algorithm is evaluated on the TEE images of five patients. First, the mitral valve apparatus and its motion are estimated from the TEE images using the machine learning method. The mitral leaflets are represented by tetrahedron finite elements with 9408 elements and 3248 vertices. Second, the mitral valve apparatus at the end diastole is loaded into the biomechanical model and the motion of the mitral annulus and the papillary tips are used as the prescribed boundary conditions. Third, the two step personalization algorithm (e.g., acts 32A and 32B of FIG. 3) is applied by adjusting the chordae rest length and material parameters from a coarse-to-fine level. The initial value of the chordae rest length is determined by the point-to-point distance from the papillary tip and the insertion points at the end systole. The initial value of the Young's modulus at the anterior and posterior leaflet is set to be 6.233 MPa and 2.087 MPa respectively.

The results of the automatic personalization at each level compared to a semi-manual patient-customization method are shown in Table 2.

TABLE 2

| (mm) | Chordae I | Chordae II | Chordae III | Chordae IV | Final | Semi-Mannual |
| --- | --- | --- | --- | --- | --- | --- |
| Patient 1 | 1.49 ± 0.83 | 1.46 ± 0.84 | 1.46 ± 0.84 | 1.46 ± 0.84 | 1.45 ± 0.84 | 1.47 ± 0.89 |
| Patient 2 | 2.98 ± 1.86 | 2.89 ± 1.88 | 2.47 ± 1.46 | 2.47 ± 1.46 | 2.47 ± 1.46 | 2.25 ± 1.27 |
| Patient 3 | 1.87 ± 1.19 | 1.87 ± 1.18 | 1.86 ± 1.17 | 1.70 ± 1.07 | 1.66 ± 1.08 | 1.91 ± 1.18 |
| Patient 4 | 1.80 ± 1.20 | 1.79 ± 1.21 | 1.79 ± 1.21 | 1.69 ± 1.14 | 1.55 ± 1.09 | 1.74 ± 1.34 |
| Patient 5 | 2.09 ± 1.36 | 2.05 ± 1.35 | 2.04 ± 1.35 | 2.04 ± 1.35 | 2.04 ± 1.35 | 2.27 ± 1.40 |

The automatic algorithm performs similarly if not better than the semi-manual method with an expert adjusting the chordae rest length and the EKF adjusting the material parameters. The average fitting error is 1.84±1.17 mm. Most patients achieve a good match at the coarse level of chordae adjustment. Some patients do not require fine tuning for the chordae. The adjustment of the chordae rest length brings the leaflet to the matching surface from the morphological perspective and reduces the average distances to about 2 mm, which is comparable to the error of the image observation from the quantitative perspective. The first step adjustment provides a better starting point to estimate the patient-specific material parameters to reduce the distance even further.

FIG. 5 shows the distances between the personalized model and the image based estimation as the ground truth in the form of a color-map from both top and side views. It can be seen that the patient-specific model simulates the mitral valve closure very closely to image based estimation. The matching is especially close in the mitral annulus region thanks to the use of the boundary conditions. The performance of the algorithm may be improved in certain regions by employing the cost function with related terms.

The estimated patient-specific material parameters are shown in table 2.

TABLE 2

| | $E_{ALf}$ | $E_{ALf}^{\perp}$ | $G_{AL}$ | $E_{PLf}$ | $E_{PLf}^{\perp}$ | $G_{PL}$ |
| --- | --- | --- | --- | --- | --- | --- |
| P1 | 6.28 | 2.37 | 2.11 | 2.21 | 1.99 | 0.74 |
| P2 | 6.23 | 2.35 | 2.09 | 2.09 | 1.89 | 0.70 |
| P3 | 5.73 | 2.16 | 1.93 | 4.58 | 4.14 | 1.54 |
| P4 | 3.60 | 1.36 | 1.21 | 2.34 | 2.11 | 0.78 |
| P5 | 6.23 | 2.35 | 2.09 | 2.09 | 1.89 | 0.70 |

The anterior leaflet shows stiffer properties compared to the posterior leaflet for all patients. The general material parameters are also the optimized estimation for two patients. Different initial values of Young's moduli are used here but reach the same estimate.

Figure 6:
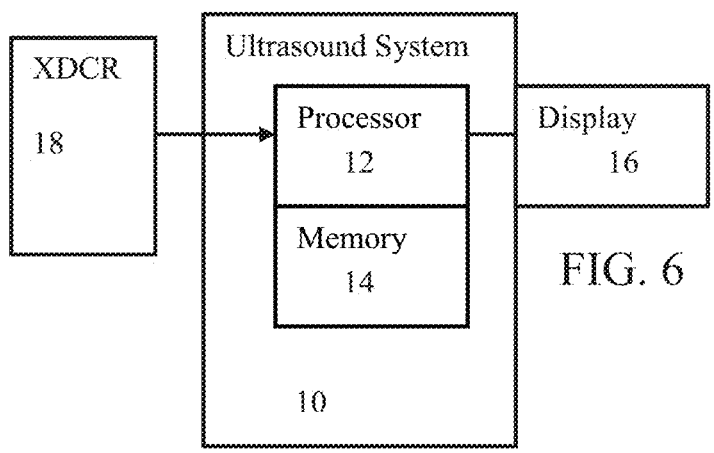
FIG. 6 is a block diagram of one embodiment of a system for estimating a mechanical property of anatomy.

FIG. 6 shows a system for estimating a mechanical property of anatomy. The system includes a transducer 18, an ultrasound scanner 10, and a display 16. The ultrasound scanner 10 includes a processor 12 and a memory 14. In alternative embodiments, the system is a CT scanner, MR scanner, or other imaging system. In yet other embodiments, the system is a workstation, computer, or server for simulating using data acquired by a separate system in real-time or using previously acquired patient-specific data stored in a memory. For example, an ultrasound scanner 10 is provided for acquiring ultrasound data representing a volume, and a separate database, server, workstation, and/or computer is provided for creating a model, detecting anatomy, and/or calculating patient-specific material properties. Additional, different, or fewer components may be used.

The ultrasound scanner 10 includes a transmit beamformer, receive beamformer, B-mode detector, Doppler detector, harmonic response detector, contrast agent detector, scan converter, filter, combinations thereof, or other now known or later developed medical diagnostic ultrasound system components. As another example, the transducer 18 is not provided, such as where the system is a workstation for off-line or later measurement of valve anatomy.

The transducer 18 is a piezoelectric or capacitive device operable to convert between acoustic and electrical energy. The transducer 18 is an array of elements, such as a multi-dimensional or two-dimensional array. Alternatively, the transducer 18 is a wobbler for mechanical scanning in one dimension and electrical scanning in another dimension. In another embodiment, the array is a one-dimensional array on a cardiac catheter or a TEE probe. Multi-dimensional arrays or a plurality of one-dimensional arrays may be provided on a TEE probe.

The ultrasound scanner 10 uses the transducer 18 to scan a heart volume of a patient. Electrical and/or mechanical steering allows transmission and reception along different scan lines in the volume. Any scan pattern may be used. For example, a plurality of different planes through the heart is scanned by rotating a TEE array, moving a catheter array, or volume scanning with a matrix array. In one embodiment, the transmit beam is wide enough for reception along a plurality of scan lines. In another embodiment, a plane, collimated or diverging transmit waveform is provided for reception along a plurality, large number (e.g., 16-64 receive beams), or all scan lines.

The scan provides the medical diagnostic ultrasound data representing the heart, part of the heart, or valve volume (e.g., mitral valve) at different times as a sequence. The scan is repeated to provide data for the volume at different times. Ultrasound data representing a volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data may be of any type, such as B-mode, flow mode (e.g., PW Doppler), spectral mode (e.g., CW Doppler), Doppler mode, contrast agent, harmonic, or other ultrasound modes of imaging.

The memory 14 is a buffer, cache, RAM, removable media, hard drive, magnetic, optical, database, or other now known or later developed memory. The memory 14 is a single device or group of two or more devices. The memory 14 is shown within the system 10, but may be outside or remote from other components of the system 10.

The memory 14 stores the ultrasound data, such as ultrasound data representing a heart or valve volume at different times in a heart cycle. The heart volume includes at least one valve, but other portions of the heart or other anatomy may be represented. The memory 14 stores flow (e.g., velocity, energy or both), spectral, and/or B-mode ultrasound data. Alternatively, the medical image data is transferred to the processor 12 from another device. The medical image ultrasound data is a three-dimensional data set, or a sequence of such sets. The data represents a three-dimensional region. Any format may be used, such as voxels interpolated to a three-dimensional grid or data representing parallel or non-parallel planes. For CW or PW Doppler, the ultrasound data may represent a volume, an area, a line, or a point.

For real-time imaging, the ultrasound data bypasses the memory 14, is temporarily stored in the memory 14, or is loaded from the memory 14. Real-time imaging may allow delay of a fraction of a second, or even seconds, between acquisition of data and imaging with measurements. For example, real-time imaging is provided by generating the images substantially simultaneously with the acquisition of the data by scanning. While scanning to acquire a next or subsequent set of data, images and measurements are generated for a previous set of data. The imaging occurs during the same imaging session or patient appointment used to acquire the data. The amount of delay between acquisition and imaging for real-time operation may vary, such as a greater delay for initially locating valve anatomies with less delay for measurements. In alternative embodiments, the ultrasound data is stored in the memory 14 from a previous imaging session and used for measuring.

The memory 14 is additionally or alternatively a non-transitory computer readable storage medium with processing instructions. The memory 14 stores data representing instructions executable by the programmed processor 12 for estimating a mechanical property of anatomy. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, three-dimensional data processor, graphics processing unit, application specific integrated circuit, field programmable gate array, digital circuit, analog circuit, combinations thereof, or other now known or later developed device for estimating a mechanical property of anatomy. The processor 12 is a single device, a plurality of devices, or a network. For more than one device, parallel or sequential division of processing may be used. Different devices making up the processor 12 may perform different functions, such as an automated anatomy detector and a separate device for performing measurements associated with the detected anatomy. In one embodiment, the processor 12 is a control processor or other processor of a medical diagnostic imaging system, such as a medical diagnostic ultrasound imaging system processor. The processor 12 is configured by or operates pursuant to stored instructions to perform various acts described herein, such as detecting anatomy, defining a biomechanical model, inversely solving for patient-specific material properties, categorizing, and/or generating and displaying an image.

In one embodiment, the processor 12 is configured by software and/or hardware to perform inverse analysis. Valve dynamics are derived from the medical diagnostic ultrasound data. The dynamics or motion may be represented by position at different times or displacement between positions at different times. The processor 12 is configured to combine the valve dynamics with a biomechanical model. The position of the valve at one time is used to load the biomechanical model. The displacement is also used as part of the biomechanical model. One or more mechanical properties of tissue of the valve of the patient are variables in the biomechanical model. As part of the inverse solution, the processor 12 estimates the mechanical property from the combination of the observed dynamics with the created biomechanical model. A difference between the observed position or displacement and the valve kinematics calculated from the biomechanical model with any currently estimated mechanical property is interpolated. The determined difference is used by the processor 12 to refine motion estimation by the biomechanical model. The currently estimated mechanical property is altered as part of the estimation, and the results of the alteration on the motion output by the biomechanical model are again compared with and differences interpolated from the observed motion or dynamics. Any inverse solution may be used for iteratively determining the mechanical property, such as the processor 12 performing the inverse solution with a Kalman filter.

The processor 12 may generate an image. The biomechanical model is used to generate an image. The patient-specific scan data may be used for imaging. The image provides a visualization of the heart or valve that is a function of the determined patient-specific mechanical property.

The display 16 is a CRT, LCD, plasma, projector, printer, or other output device for showing an image. The display 16 displays an image of the detected anatomy, such as an image of a valve rendered from medical data and overlaid or highlighted based on the estimates of the valve position and/or mechanical property. The display 16 displays a sequence of renderings to generate a visualization of the valve motion through the sequence. The visualization may be generated during a same examination session as the scan. The detected anatomy may or may not be segmented, such as just displaying the valve.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for determining a mechanical property of anatomy, the method comprising:

determining, by a processor, first anatomy locations of a valve of a patient derived from first medical scan data of the patient at a first time;

determining, by the processor, second anatomy locations of the valve of the patient from second medical scan data of the patient at a second time different than the first time, the second anatomy locations being for a same anatomy of the valve as the first anatomy locations;

deriving, by the processor, an actual displacement between the first anatomy locations and the second anatomy locations;

modeling, by the processor, the valve with a biomechanical model, which is a function of the mechanical property and the actual displacement;

determining, by the processor based on the biomechanical model, first modeled anatomy locations and second modeled anatomy locations;

deriving, by the processor, a modeled displacement between the first modeled anatomy locations and the second modeled anatomy locations; and inversely solving, by the processor, for a value of the mechanical property of the valve as a function of the biomechanical model and a comparison of the actual displacement with the modeled displacement.

2. The method of claim 1 wherein determining the first and second anatomy locations comprises determining from ultrasound data representing a volume including the valve over time.

3. The method of claim 1 wherein determining the first and second anatomy locations comprises determining by application of the first and second medical scan data, respectively, as input features to a machine-learning algorithm.

4. The method of claim 1 wherein determining the first and second anatomy locations comprises determining as a function of a discriminative probabilistic model.

5. The method of claim 1 wherein determining the first and second anatomy locations comprises determining locations for anterior and posterior papillary tips, mitral annulus, and anterior and posterior leaflets at the first and second times and determining a mesh for the valve at the first and second times.

6. The method of claim 1 wherein modeling comprises modeling with the biomechanical model comprising a finite element model.

7. The method of claim 1 wherein modeling comprises modeling with the biomechanical model comprising a dynamic system having mass, damping, stiffness, displacement, velocity, and acceleration terms.

8. The method of claim 1 wherein solving comprises solving for the value of a Young's modulus of the valve of the patient in-vivo from the first and second medical scan data of the patient.

9. The method of claim 1 wherein solving comprises solving for values of chordae lengths, respectively, of the valve of the patient in-vivo from the first and second medical scan data of the patient.

10. The method of claim 1 wherein solving for the value comprises solving for the value of the mechanical property and values of a plurality of other mechanical properties of the valve of the patient.

11. The method of claim 1 wherein solving for the value of the mechanical property of the valve of the patient comprises solving from the biomechanical model, the displacement from the first and second medical scan data of the patient and the modeled displacement.

12. The method of claim 1 wherein solving comprises solving as a non-linear function of the mechanical property to the first and second anatomy locations and with an extended Kalman filter.

13. The method of claim 1 wherein solving comprises solving as a function of a fluid-structure interaction model incorporating the biomechanical model, wherein the solving further comprises solving for a pressure with the fluid-structure interaction model.

14. The method of claim 1 further comprising categorizing a condition of the valve of the patient based on a comparison of the value of the mechanical property with a pre-determined value of the mechanical property.

15. The method of claim 1 further comprising displaying an image, the imaging being a function of the value of the mechanical property.

16. In a non-transitory computer readable storage medium having stored therein data representing instructions executable by a programmed processor for determining a mechanical property of anatomy, the storage medium comprising instructions for:

deriving an actual motion of the anatomy from scan data of a patient;

calculating a modeled motion of the anatomy from a biomechanical model, the biomechanical model being a function of the actual motion and at least one patient-specific material parameter;

comparing the modeled motion to the actual motion; and solving, iteratively, for the patient-specific material parameter by repetition of the calculating and comparing.

17. The non-transitory computer readable storage medium of claim 16 wherein the anatomy comprises a heart valve, and wherein solving comprises solving for at least one Young's modulus of the heart valve and at least two chordae lengths of the heart valve.

18. The non-transitory computer readable storage medium of claim 16 wherein deriving the actual motion comprises deriving from ultrasound data input to a discriminative probabilistic model, wherein calculating with the biomechanical model comprises simulating biomechanics with finite element analysis, and wherein solving comprises solving with Kalman filtering.

19. A system for estimating a mechanical property of anatomy, the system comprising:

an ultrasound scanner configured to scan a heart volume of a patient, the scan providing medical diagnostic ultrasound data representing at least a part of the heart;

a processor configured to perform inverse analysis by deriving actual valve dynamics from the medical diagnostic ultrasound data, combining the actual valve dynamics with a biomechanical model, deriving modeled valve dynamics from the combination, estimating the mechanical property from the combination and the derived modeled valve dynamics, interpolating valve kinematics with the estimated mechanical property, and refining motion estimation with an alteration of the mechanical property; and a display configured to generate a visualization of the mechanical property.

20. The system of claim 19 wherein the processor is configured to perform the refining with a Kalman filter.

* * * * *